(12) United States Patent
Wasserscheid et al.

(10) Patent No.: US 7,553,406 B2
(45) Date of Patent: Jun. 30, 2009

(54) PROCESS FOR REMOVING POLAR IMPURITIES FROM HYDROCARBONS AND MIXTURES OF HYDROCARBONS

(75) Inventors: Peter Wasserscheid, Erlangen (DE); Andreas Bösmann, Stegen (DE); Andreas Jess, Bayreuth (DE); Leonid Datsevich, Bayreuth (DE); Christoph Schmitz, Jüchen (DE); Andrea Wendt, Königstein-Taunus (DE)

(73) Assignee: Merck Patent GmbH, Darmstadt (DE)

( * ) Notice: Subject to any disclaimer, the term of this patent is extended or adjusted under 35 U.S.C. 154(b) by 530 days.

(21) Appl. No.: 10/836,106

(22) Filed: Apr. 30, 2004

(65) Prior Publication Data

US 2005/0010076 A1    Jan. 13, 2005

Related U.S. Application Data

(63) Continuation-in-part of application No. PCT/EP02/12239, filed on Nov. 2, 2002.

(30) Foreign Application Priority Data

Nov. 8, 2001    (DE) ................ 101 55 281

(51) Int. Cl.
*C10G 29/20*    (2006.01)
*C10M 169/04*    (2006.01)
*C07C 7/10*    (2006.01)

(52) U.S. Cl. ............. 208/236; 208/237; 208/262.1; 585/1; 585/860; 585/864; 585/865; 585/867

(58) Field of Classification Search ............ 208/208 R, 208/236, 237, 262.1; 585/833, 851, 856, 585/860, 861, 862, 864, 865, 866, 867
See application file for complete search history.

(56) References Cited

U.S. PATENT DOCUMENTS

| 5,057,207 | A | * | 10/1991 | Basler ................ 208/262.1 |
| 5,494,572 | A | * | 2/1996 | Horii et al. ............ 208/237 |
| 5,744,024 | A | * | 4/1998 | Sullivan et al. ........ 208/237 |
| 6,274,026 | B1 | * | 8/2001 | Schucker et al. ....... 205/696 |
| 6,319,428 | B1 | * | 11/2001 | Michot et al. ......... 252/500 |
| 7,001,504 | B2 | * | 2/2006 | Schoonover ........... 208/236 |
| 2003/0085156 | A1 | | 5/2003 | Schoonover | |

FOREIGN PATENT DOCUMENTS

| DE | 767 891 | 7/1954 |
| WO | WO 01/40150 A1 | 6/2001 |
| WO | WO 01/55060 A2 | 8/2001 |

OTHER PUBLICATIONS

Bössman et al. ("Deep desulfurization of diesel fuel by extraction with ionic liquids", Chem. Commun. (2001), 2494-2495).

* cited by examiner

*Primary Examiner*—Glenn Caldarola
*Assistant Examiner*—Randy Boyer
(74) *Attorney, Agent, or Firm*—Rick Matos; Innovar, L.L.C.

(57) ABSTRACT

This invention relates to a process for removing polarizable impurities from hydrocarbons and mixtures of hydrocarbons using ionic liquids as an extraction medium. By way of extraction, the degree of contamination of the hydrocarbon or mixture of hydrocarbons is reduced to a low or very low level. The specific ionic liquids are compounds of the Formula 1, which are organic salts that are liquid or can be melted to form a liquid and that can form at least a biphasic mixture with a hydrocarbon. The process is suitable for purifying a wide range of hydrocarbons under a wide range of process conditions.

58 Claims, No Drawings

PROCESS FOR REMOVING POLAR IMPURITIES FROM HYDROCARBONS AND MIXTURES OF HYDROCARBONS

CROSS REFERENCE TO EARLIER FILED APPLICATIONS

The present application is a CONTINUATION-IN-PART of PCT International Application Serial No. PCT/EP02/12239 filed Nov. 2, 2002 and published as PCT International Publication No. WO 03/037835 on May 8, 2003, which claims the benefit of priority of German Patent Application Serial No. DE 101 55 281.5 filed Nov. 8, 2001, the entire disclosures of which are hereby incorporated by reference.

FIELD OF THE INVENTION

This invention relates to a process for removing polar impurities from hydrocarbons and mixtures of hydrocarbons using organic ionic liquids as an extraction medium for reducing the concentration of contaminants in the hydrocarbon or mixture of hydrocarbons to a low or very low level.

BACKGROUND OF THE INVENTION

The separation of polar (or polarizable) impurities from hydrocarbons or mixtures of hydrocarbons to reduce their contents to ppm (parts per million) levels is of great technical importance but is often found to pose significant technical problems. The importance of such purification processes resides in the fact that many polarizable impurities in hydrocarbons and mixtures of hydrocarbons limit their technical usefulness because the impurities have either disturbing effects on the actual technical process using the hydrocarbon or because they result in the formation of by-products, which are undesirable from an environmental point of view. Important examples thereof include the separation of sulfur and nitrogen components from fuels for reducing the $SO_2$ emissions or the reduction of chlorine-containing compounds from motor oils to avoid corrosion problems.

The deep desulfurization of fuels to achieve very low sulfur contents (>50 ppm) is a great problem in the production of fuel. Regulations currently require a reduction of the sulfur content in gasoline and diesel fuels to 50 ppm for the year 2005 within the European Union. Propositions by the German government already aim at a reduction to 10 ppm in the year 2003 (W. Bonse-Geuking, Erdöl Erdgas Kohle, 116, 9 (2000) 407). According to the current state of the art, the separation of sulfur-containing compounds is effected by catalytic hydrogenation in refineries (J. Pachano, J. Guitian, O. Rodriguez, J. H. Krasuk (Intevep, S. A.), U.S. Pat. No. 4,752,376 (1988), Jr. Hensley, L. Albert, L. M. Quick (Standard Oil Company), U.S. Pat. No. 4,212,729 (1980), S. B. Alpert, R. H. Wolk, M. C. Chervenak, G. Nongbri (Hydrocarbon Research, Inc.), U.S. Pat. No. 3,725,251 (1971), G. R. Wilson (Gulf Research & Development Company), U.S. Pat. No. 3,898,155 (1975), Y. Fukui, Y. Shiroto, M. Ando, Y. Homma (Chiyoda Chemical Engineering & Construction Co., Ltd.), U.S. Pat. No. 4,166,026 (1979), R. H. Fischer, J. Ciric, T. E. Whyte (Mobil Oil Corporation), U.S. Pat. No. 3,867,282 (1975), J. G. Gatsis (Universal Oil Products Company), U.S. Pat. No. 3,859,199 (1975), L. K. Riley, W. H. Sawyer (Esso Research and Engineering Company), U.S. Pat. No. 3,770,617 (1973), C. E. Adams, W. T. House (Esso Research and Engineering Company), U.S. Pat. No. 3,668,116 (1972)). The separation of the hydrogen sulfide formed is effected by amine washers (W. W. Kensell, M. P. Quinlan, The M. W. Kellogg Company Refinery Sulfur Management, in: R. A. Meyers (Ed.), Handbook of Petroleum Refining Processes, New York, San Francisco, Washington, D.C., Auckland, Bogota, Caracas, Lisbon, London, Madrid, Mexico City, Milan, Montreal, New Delhi, San Juan, Singapore, Sydney, Tokyo, Toronto: McGraw-Hill, 1996, 11.3). Another method is the UOP Merox process. In this process, the mercaptans present in the fuel are reacted with oxygen to form disulfides in the presence of an organometallic catalyst at low temperatures in an alkaline medium (D. L. Holbrook, UOP Merox Process, in: R. A. Meyers (Ed.), Handbook of Petroleum Refining Processes, New York, San Francisco, Washington, D.C., Auckland, Bogota, Caracas, Lisbon, London, Madrid, Mexico City, Milan, Montreal, New Delhi, San Juan, Singapore, Sydney, Tokyo, Toronto: McGraw-Hill, 1996, 11.29).

Halogenated impurities in hydrocarbons and mixtures of hydrocarbons cause corrosion problems in engineering, and therefore, their content must usually be reduced down to a range of a few ppm. This can be achieved by catalytic hydrogenation or electrolytic dehalogenation (G. Scharfe, R.-E. Wilhelms (Bayer Aktiengesellschaft), U.S. Pat. No. 3,892,818 (1975), J. Langhoff, A. Jankowski, K.-D. Dohms (Ruhrkohle A G), U.S. Pat. No. 5,015,457 (1991), W. Dohler, R. Holighaus, K. Niemann (Veba Oel Aktiengesellschaft), U.S. Pat. No. 4,810,365 (1989), F. F. Oricchio (The Badger Company, Inc.), U.S. Pat. No. 3,855,347 (1974), R. W. La Hue, C. B. Hogg (Catalysts and Chemicals, Inc.), U.S. Pat. No. 3,935,295 (1976), F. Rasouli, E. K. Krug (ElectroCom Gard, Ltd.), U.S. Pat. No. 5,332,496 (1994), H. J. Byker (PCB Sandpiper, Inc.), U.S. Pat. No. 4,659,443 (1987), J. A. F. Kitchens (Atlantic Research Corporation), U.S. Pat. No. 4,144,152 (1979)). However, catalytic hydrogenation is not desirable on a large scale and there is a need for efficient yet more cost effective processes to remove halogenated impurities from hydrocarbons.

Ionic liquids have been known for many years (P. Wasserscheid, W. Keim, Angew. Chem., 112 (2000) 3926; T. Welton, Chem. Rev., 99 (1999) 2071; J. D. Holbrey, K. R. Seddon, Clean Products and Processes, 1 (1999), 223). They are characterized by being liquids that consist exclusively, or substantially exclusively, of ions. Important properties include their solubility properties, which can be adjusted within wide limits by varying the cation and/or anion, and their extremely low vapor pressure. Numerous ionic liquids are not completely miscible with hydrocarbons and mixtures of hydrocarbons, i.e., the formation of two-phase or multi-phase systems occurs (P. Wasserscheid, W. Keim, Angew. Chem., 112 (2000) 3926).

In view of the above, there is an immediate need for efficient and costs effective processes for the removal of impurities, such as polar or polarizable impurities, from useful hydrocarbons or hydrocarbon mixtures.

SUMMARY OF THE INVENTION

The invention represents a novel and extremely efficient solution to the above mentioned problems in the separation of polar or polarizable impurities from hydrocarbons or mixtures of hydrocarbons. The invention is based on the surprising finding that the content of polarizable impurities in a hydrocarbon or mixture of hydrocarbons can be significantly reduced by extracting the impurity(ies) from the hydrocarbon or mixture of hydrocarbons with an organic ionic liquid or a mixture of organic ionic liquids, provided the ionic liquid employed exhibits a miscibility gap with the hydrocarbon or mixture of hydrocarbons. The invention provides a process by way of which a hydrocarbon, or mixture thereof, is treated with an organic ionic liquid, as defined herein, to form an at least biphasic mixture. During treatment, the hydrocarbon and organic ionic liquid are agitated to improve the extraction of the impurity(ies) from the hydrocarbon. The phases are then separated, thereby forming a hydrocarbon having a decreased concentration of impurity(ies). The hydrocarbon can be exposed to the ionic liquid any number of times as required to reduce the level of impurity(ies) in the hydrocarbon to the desired concentration. However, during each extraction step, the ionic liquid and hydrocarbon must be able to form at least two separable phases.

The benefits of the novel extraction technology which is here described are very mild process conditions, high efficiency in removal of impurities, cost reduction and an environmental benign process.

The organic ionic liquid must be able to form at least a biphasic mixture with a hydrocarbon being purified in order to permit separation of the ionic liquid and impurity(ies) from the hydrocarbon. The mixture of phases can be a combination of liquid phases or a combination of solid and liquid phases. As such, an ionic liquid is said to possess a miscibility gap with the hydrocarbon or mixture of hydrocarbons. Below its melting point, an ionic liquid of the invention may be present as an ionic solid. The organic ionic liquid comprises an organic cation and an organic anion. The identity of the organic anion and organic cation is independently selected at each occurrence such that the organic ionic liquid comprises one or more organic cations and one or more organic anions.

The organic ionic liquid employed is a compound or mixture of compounds of Formula 1

  Formula 1 wherein:

n=1 or 2;

the anion $(Y)^{n-}$ is selected from the group consisting of tetrafluoroborate $((BF_4)^-)$, tetrachloroborate $((BCl_4)^-)$, hexafluorophosphate $((PF_6)^-)$, hexafluoroantimonate $((SbF_6)^-)$, hexafluoroarsenate $((AsF_6)^-)$, tetrachloroaluminate $((AlCl_4)^-)$, trichlorozincate $((ZnCl_3)^-)$, dichlorocuprate, sulfate $((SO_4)^{2-})$, carbonate $((CO_3)^{2-})$, fluorosulfonate, $(R'—COO)^-$, $(R'—SO_4)^-$, $(R'—SO_3)^-$ or $((R'—SO_2)_2N)^-$, wherein R' is a linear or branched aliphatic or alicyclic alkyl containing from 1 to 16 carbon atoms, or a $C_5$-$C_{18}$ aryl, $C_5$-$C_{18}$-aryl-$C_1$-$C_6$-alkyl or $C_1$-$C_6$-alkyl-$C_5$-$C_{18}$-aryl residue which may be substituted with halogen atoms;

the cation $(A)^+$ is selected from the group consisting of
quaternary ammonium cations of general formula $(NR^1R^2R^3R)^+$, phosphonium cations of general formula $(PR^1R^2R^3R)^+$, imidazolium cations of general formula

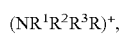

wherein the imidazole nucleus may be substituted with at least one group selected from $C_1$-$C_6$ alkyl, $C_1$-$C_6$ alkoxy, $C_1$-$C_6$ aminoalkyl, $C_5$-$C_{16}$ aryl or $C_5$-$C_{16}$-allyl-$C_1$-$C_6$-alkyl groups;

pyridinium cations of general formula

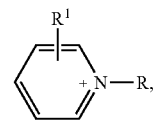

wherein the pyridine nucleus may be substituted with at least one group selected from $C_1$-$C_6$ alkyl, $C_1$-$C_6$ alkoxy, $C_1$-$C_6$ aminoalkyl, $C_5$-$C_{16}$ aryl or $C_5$-$C_{16}$-aryl-$C_1$-$C_6$-alkyl groups;

pyrazolium cations of general formula

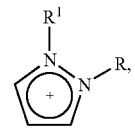

wherein the pyrazole nucleus may be substituted with at least one group selected from $C_1$-$C_6$ alkyl, $C_1$-$C_6$ alkoxy, $C_1$-$C_6$ aminoalkyl, $C_5$-$C_{16}$ aryl or $C_5$-$C_{16}$-aryl-$C_1$-$C_6$-alkyl groups; and triazolium cations of general formula

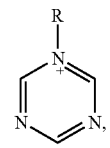

wherein the triazole nucleus may be substituted with at least one group selected from $C_1$-$C_6$ alkyl, $C_1$-$C_6$ alkoxy, $C_1$-$C_6$ aminoalkyl, $C_5$-$C_{16}$ aryl or $C_5$-$C_{16}$-aryl-$C_1$-$C_6$-alkyl groups;

the residues $R^1$, $R^2$, $R^3$ are independently selected from the group consisting of hydrogen;

linear or branched, saturated or unsaturated, aliphatic or alicyclic alkyl groups having from 1 to 20 carbon atoms;

heteroaryl, heteroaryl-$C_1$-$C_6$-alkyl groups having from 3 to 8 carbon atoms in the heteroaryl residue and at least one heteroatom selected from N, O and S which may be substituted with at least one group selected from $C_1$-$C_6$ alkyl groups and/or halogen atoms; and aryl, aryl-$C_1$-$C_6$-alkyl groups having from 5 to 16 carbon atoms in the aryl residue which may be optionally substituted with at least one $C_1$-$C_6$ alkyl group and/or halogen atom; and the residue R is selected from the group consisting of linear or branched, saturated or unsaturated, aliphatic or alicyclic alkyl groups having from 1 to 20 carbon atoms;

heteroaryl, heteroaryl-$C_1$-$C_6$-alkyl groups having from 3 to 8 carbon atoms in the heteroaryl residue and at least one heteroatom selected from N, O and S which may be substituted with at least one group selected from $C_1$-$C_6$ alkyl groups and/or halogen atoms;

aryl, aryl-$C_1$-$C_6$-alkyl groups having from 5 to 16 carbon atoms in the aryl residue which may be optionally substituted with at least one $C_1$-$C_6$ alkyl group and/or halogen atom.

The cation $(A)_n^+$ can be prepared by alkylation of the underlying amines, phosphines, imidazoles, pyridines, triazoles and pyrazoles with an organohalide RX and replacement of the halide anion $X^-$ with the above defined anion $(Y)^-$ or (Y)$^{2-}$. The ionic liquid can be prepared with or without isolation of the intermediate products, e.g. with or without isolation of the alkylated amine halide salts (A)$_n$$^+$(X)$_n$$^-$.

One aspect of the invention provides a process for the purification of (removal of impurity(ies) from or reduction of the concentration of impurity(ies) in) a hydrocarbon, or mixture of hydrocarbons, the process comprising the steps of:

providing a hydrocarbon, or mixture of hydrocarbons, comprising one or more impurities that are extractable with an ionic liquid;

exposing the hydrocarbon, or mixture thereof, to an ionic liquid while agitating for a period of time sufficient and at a temperature sufficient for the ionic liquid to extract a portion of the one or more impurities from and to form an at least biphasic mixture with the hydrocarbon, or mixture thereof; and separating the ionic liquid from the hydrocarbon, or mixture thereof, whereby the amount of one or more impurities in the hydrocarbon, or mixture thereof, is reduced; wherein:

the ionic liquid is a compound, or a mixture of compounds, of the Formula 1, as defined herein.

Specific embodiments include those wherein: 1) the step of exposing is conducted while heating; 2) the ionic liquid is a solid at <30° C.; 3) the ionic liquid is a liquid at >0° C.; 4) the impurity is a sulfur-containing or halogen-containing impurity; 5) the steps of exposing and separating are repeated; 6) the ionic liquid is a solid in the absence of added heat.

The invention also provides a purified hydrocarbon, or mixture of hydrocarbons, prepared according to the extraction method of the invention, wherein a hydrocarbon, or mixture thereof, comprising one or more impurities is treated with one or more ionic liquids, as defined herein, to provide the purified hydrocarbon, or mixture of hydrocarbons, having a reduced amount of the one or more impurities.

Another aspect of the invention provides an at least biphasic composition comprising a hydrocarbon, or mixture of hydrocarbons, one or more polar impurities, and one or more ionic liquids of the Formula 1, wherein a first phase comprises the hydrocarbon, or mixture of hydrocarbons; a second phase comprises the one or more ionic liquids; and the one or more polar impurities is located in the first phase, second phase or both phases. Specific embodiments include those wherein: 1) the one or more ionic liquids is present as an extraction medium; and 2) the one or more ionic liquid is present as a component in a reaction medium.

In a further aspect the invention relates to a composition comprising a hydrocarbon or mixture of hydrocarbons as well as at least one of the ionic liquids as defined above. These compositions can be used as the starting point for performing the extraction described herein. Accordingly, the compositions according to the invention may also contain a wide variety of substrates, valuable substances or impurities in addition to said hydrocarbon or mixture of hydrocarbons.

DETAILED DESCRIPTION OF THE INVENTION

As used herein, the terms polar and polarizable are used interchangeably and refer to compounds that are polar in nature or can be made polar by changing the conditions of the environment in which they are found.

In particular embodiments of the invention, the alkyl-, aryl-, arylalkyl-, alkoxy- and alkylarylsulfonate groups (anion (Y)) may be substituted with halogen atoms, especially fluorine, chlorine or bromine. Particularly preferred are the fluorinated, especially perfluorinated, alkyl- and above-mentioned arylsulfonates, such as trifluoromethanesulfonate (triflate). As non-halogenated members there may be mentioned the methanesulfonate, benzenesulfonate and toluenesulfonate groups as well as all other sulfonate leaving groups known in the prior art.

In a further embodiment of the invention, the alkyl-, aryl-, arylalkyl-, alkoxy- and alkylarylcarboxylate groups may be substituted with halogen atoms, especially fluorine, chlorine or bromine. Particularly preferred are the fluorinated, especially perfluorinated, alkyl- and above-mentioned arylcarboxylates, such as trifluoromethanecarboxylate (trifluoroacetate; CF$_3$COO$^-$). As non-halogenated members there may be mentioned the acetate and benzoate groups as well as all other carboxylate leaving groups known in the prior art.

In preferred embodiments of the invention, the $C_1$-$C_6$ alkyl groups mentioned in connection with the substituents may be independently replaced with $C_2$-$C_4$ alkyl groups. Also, the $C_1$-$C_6$ alkoxy groups mentioned in connection with the substituents may be independently replaced with $C_2$-$C_4$ alkoxy groups. In a further alternative of the invention, the $C_5$-$C_{16}$ aryl groups mentioned in connection with the substituents may be independently replaced by $C_6$-$C_{10}$ aryl groups, and the $C_3$-$C_8$ heteroaryl groups may be independently replaced with $C_3$-$C_6$ heteroaryl groups. The halogen atoms with which the alkyl, alkoxy and aryl groups may be substituted are selected from fluorine, chlorine, bromine and iodine, preferably fluorine, chlorine and bromine.

In another preferred embodiment, the residue R' is a linear or branched aliphatic or alicyclic alkyl containing from 1 to 8 carbon atoms, or a $C_6$-$C_{10}$ aryl, $C_6$-$C_{10}$-aryl-$C_1$-$C_4$-alkyl or $C_1$-$C_4$-alkyl-$C_6$-$C_{10}$-aryl residue which may be substituted with halogen atoms.

The cations (A) are selected, by way of example and without limitation, from cocoalkylpentaethoxymethylammonium, ($C_{12}$-$C_{18}$)Alkylpoly(3)oxyethldihydroxy-ethylmethylammonium, trimethylphenylammonium, methyltrioctylammonium, benzyldimethyltetradecylammonium, tetrabutylphosphonium, trihexyl(tetradecyl)phosphonium, 3-butyl-1-methylimidazolium, 3-ethyl-1-methylimidazolium, N-butyl-pyridinium, N-ethylpyridinium, diethylpyrazolium, 1-ethyl-3-methylimidazolium, 1-butyl-3-methylimidazolium, 1-hexyl-3-methylimidazolium, 1-octyl-3-methylimidazolium, 1-decyl-3-methylimidazolium, 1-butyl-4-methylpyridinium, 1-butyl-3-methylpyridinium, 1-butyl-2-methylpyridinium, 1-butylpyridinium, 1-butylmethylimidazolium, nonylmethylimidazolium, butylmethylimidazolium, hexylmethylimidazolium, octylmethylimidazolium, 4-methylbutylpyridinium, triethylammonium, trieethylmethylammonium, butylmethylpyridinium, propylammonium, methylmethylimidazolium, ethylmethylimidazolium, butylmethylimidazolium and butylmethylimidazolium.

In an embodiment of the process according to the invention, the ionic liquid is employed as a sole extraction medium, i.e., free from other extraction media. For example, the mixture of hydrocarbon and ionic liquid does not include another solvent or extraction medium. In this case, the impurity(ies) is(are) extracted from the hydrocarbon into the ionic liquid.

In another embodiment, the ionic liquid is included in a reaction medium (defined as a mixture of the hydrocarbon, at least one other substrate involved in a chemical reaction, and the ionic liquid). In this case, the ionic liquid is present while another process is occurring in the hydrocarbon. At an appropriate time, the reaction is stopped and the mixture is allowed to separated into individual phases comprising the hydrocarbon phase and the ionic liquid phase. The phases are then separated, whereby a purer form of the hydrocarbon is prepared.

The proportion of the ionic liquid in the reaction medium or extraction mixture (defined as a mixture of the ionic liquid and the hydrocarbon) may be between 0.0001 and 99.9% by volume, preferably between 0.1 and 50% by volume, more preferably between 0.5 and 30% by volume, based on the total amount of the reaction medium or extraction mixture. The mass ratio of the ionic liquid to hydrocarbon can vary within the range of 1:1,000,000 to 999:1, or 1:10 to 1:1 or 1:2 to 1:3.

In addition to the ionic liquid, the extraction mixture may also contain one or more further extractants. It is only necessary that the extraction mixture be able to form at least two separate phases at some point during the extraction process: a first phase comprising the hydrocarbon, or mixture thereof, and a second phase comprising the ionic liquid, it being understood that the amount or concentration of impurity(ies) in each of the phases will vary according to the number of times the hydrocarbon has been extracted with the ionic liquid, the affinity that the ionic liquid has for the impurity, the solubility of the impurity in the hydrocarbon and ionic liquid, and the initial concentration of the impurity in the hydrocarbon.

These other extractants may be selected from the group consisting of water, buffer solutions (pH 2 to 10, preferably 5 to 8) and organic solvents. Organic solvents suitable for use are miscible with water or immiscible with water. In principle, all conventional extractants (solvents) known in the field of liquid-liquid, liquid-solid, or solid-liquid extractions may be used. Examples of organic solvents include, by way of example and without limitation, methyl tert-butyl ether, toluene, hexane, heptane, tert-butanol, glycols, and polyalkyleneglycols.

Suitable ether solvents include: dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, or t-butyl ethyl ether.

Suitable protic solvents may include, by way of example and without limitation, water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, anisole, benzyl alcohol, phenol, or glycerol.

Suitable hydrocarbon solvents include: benzene, cyclohexane, pentane, cycloheptane, methylcyclohexane, heptane, ethylbenzene, m-, o-, or p-xylene, octane, indane, nonane, or naphthalene.

The properties of the extraction media can be tailored by using a mixture of two or more ionic liquids. Different ionic liquids show different extractive properties for different polarizable compounds. The impurities in the ionic liquid, as described above, have a significant effect of their behavior. A combination of ionic liquids and water, buffer solution or organic solvents can be used to extract two or more polarizable impurities at a time.

The medium to be extracted is represented by a hydrocarbon or mixture of hydrocarbons including one or more ionic liquid-extractable impurities (meaning impurities that are extractable with an ionic liquid according to the invention). As an example, the separation of sulfur and nitrogen components (characterized as ionic liquid-extractable impurities) from fuels for reducing the $SO_2$ emissions, or the reduction of chlorine-containing compounds (characterized as ionic liquid-extractable impurities) from motor oils to avoid corrosion problems may be mentioned. While the above examples include hydrocarbons such as gasoline, diesel, kerosene, and oil, the invention is also useful for extracting impurities from other hydrocarbons including, by way of example and without limitation, fuel oil, lubricating oil, shale oil, brake fluid, hydraulic fluid, power steering fluid, light atmospheric gas oil, crude oil, heavy atmospheric gas oil, vacuum gas oil, FCC light cycle oil, coker gas oil, or naphtha.

Aliphatic or aromatic hydrocarbons from gases to wax or tar with a melting below 200° C. are purified with an ionic liquid according to the invention. In particular, mixtures of these compounds which are typically found in natural gas, naptha, diesel oil, FCC, or other boiling fraction of a refinery. Also, a mixture of hydrocarbons from a Fischer-Troppsch process can be purified according to the invention.

Both leaded and unleaded fuels can be extracted according to the invention. Exemplary fuels are sold under the following brand names: BP Racing Fuel, ELF Racing Fuel—Moto 124, Shell Racing Fuel 100, Shell Racing Fuel A, Sunoco—Standard, Sunoco—Supreme, Sunoco—Supreme NOS, Sunoco—Maximal, Sunoco—Maximal #5, Sunoco—GT 100, Sunoco—GT Plus, VP 110—AU—SGFO, VP C14+—AU—SGFO, VP C16—AU—BGFO, VP C25—AU—AU-RGFO, VP Motorsport 103 AU, or VP SV0.5 AU.

In principle, the substances to be extracted may be any polar or polarizable compounds. As examples, there may be mentioned sulfur-containing, nitrogen-containing, oxygen-containing and halogen-containing compounds. Extractable polar (or polarizable) impurities include sulphur and sulphur-containing compounds such as, by way of example and without limitation, organic aliphatic or aromatic sulphur compounds, mercaptane, thiophene, methylthiophene, dibenzothiophene; nitrogen-containing compounds such as, by way of example and without limitation, ammonia, organic nitrogen compounds, amides, amino acids, and N-heterocyclic compounds; oxygen-containing compounds such as, by way of example and without limitation, aldehydes, ketones, carboxylic acids, peroxides and organohalides especially organochlorides and chlor, and inorganic chlorides.

According to the invention, it was found that the extraction of sulfur-containing impurities from hydrocarbons or mixtures of hydrocarbons by means of ionic liquids or a mixture of ionic liquids offers significant advantages over hydrogenation methods used according to the current state of the art. The advantages relate to the minimization of hydrogen consumption, reduction of the operational and investment costs down to 50% and the achievement of absolute minimum limits of the medium to be extracted, in contrast to the prior art. For example, if the process according to this invention is applied to the desulfurization of diesel fuel, the extraction of the sulfur-containing impurities by means of ionic liquids is substituted for the currently applied hydrogenation reactions. The process according to this invention is not limited to any particular classes of sulfur-containing compounds, but universally reduces the content of sulfur-containing compounds in the processing of petrol fractions. By employing several extraction steps, the residual sulfur content can be reduced down to below the detection limit of the analytical method employed (<1 ppm). Thus, the process according to this invention represents a method for significantly reducing the sulfur content in different fuels and to clearly reduce it below the future legal level of 50 ppm. In one embodiment, the concentration of polar impurities in the hydrocarbon after completion of extraction with an ionic liquid is less than 1000 ppm, less than 500 ppm, less than 250 ppm, less than 125 ppm, less than 50 ppm, or less than 25 ppm.

The process according to the invention can be performed at temperatures of from −150° C. to 500° C., preferably within a temperature range of from −25° C. to 200° C., more preferably within a temperature range of from 0° C. to 150° C. The temperature at which the process is conducted will vary according to the identity and physical properties of the ionic liquid and the hydrocarbon. The process can be performed in a temperature range in which the ionic liquids are in either liquid or solid form, meaning that the extraction can be conducted as a liquid-liquid or liquid-solid (hydrocarbon-ionic liquid) extraction. The ionic "liquid" of the invention can actually exist as a solid or liquid depending upon the temperature of the environment to which it is exposed. In either case, the extraction of the invention is conducted under conditions such that the ionic "liquid" exists as an actual liquid rather than as a solid. Phase separation can be conducted, however, such that the ionic "liquid" is either a true liquid or a solid. For example, if an ionic solid must be melted to form an actual liquid, then it might be separated from the hydrocarbon in liquid form or, upon cooling, in solid form. On the other hand, the extraction can be performed by exposing the hydrocarbon to an ionic solid, whereby impurities are extracted into the solid, following which the mixture of solid and impurities is easily separated from the hydrocarbon by any means known useful for the separation of solids from liquids, e.g. centrifugation, decantation, precipitation, filtration, etc. During the application every ionic liquid will be used in their liquid state. Therefore the extraction temperature can be vary between −150° and 500° C.

An extraction process can be performed discontinuously by means of a stirred tank or continuously by means of a mixer-settler unit, tray column, bubble column, packed column, disk separator, rotating disk column or vibrating plate column.

The ionic liquid can be recovered by removal of impurities therefrom, the impurities having been obtained by extraction thereof from a hydrocarbon. The recover of ionic liquid is suitably done by re-extraction of the impurity, e.g. sulfur compound, with a medium that exhibits a miscibility gap with the ionic liquid but which is also very volatile. For example, the separation of the extracted substrates (or impurities) from the ionic liquid can be effected by extraction with or without previous hydrogenation or oxidation, with another hydrocarbon or mixture of hydrocarbons, with an organic compound or mixture of organic compounds, with liquid carbon dioxide, with supercritical carbon dioxide, with liquid propane or supercritical propane followed by distillation, by steam distillation, by sublimation or by absorption of the impurity or substrate to an absorbent (e.g., active charcoal or zeolite). The ionic liquid purified as above can be recycled into the hydrocarbon extraction process, e.g. the process of desulfurization of a hydrocarbon.

In the removal of halogenated compound(s) from a hydrocarbon, herein referred to as a dehalogenation process, the process of the invention circumvents the classical drawbacks of conventional dehalogenation by hydrogenation (high pressure, high temperatures, release of corrosive HCl gas).

The above-mentioned ionic liquids are prepared according to the procedures described in the following examples. In view of the above description and the examples below, one of ordinary skill in the art will be able to practice the invention as claimed without undue experimentation. The foregoing will be better understood with reference to the following examples that detail certain procedures for the preparation of formulations according to the present invention. All references made to these examples are for the purposes of illustration. The following examples should not be considered exhaustive, but merely illustrative of only a few of the many embodiments contemplated by the present invention.

Example 1

Desulfurization of a Hydrocarbon by Removal of a Sulfur-Containing Impurity

The following general procedure is used for the desulfurization of a hydrocarbon.

A hydrocarbon liquid comprising a sulfur-containing impurity is exposed to an ionic liquid according to the invention while agitating the mixture. Following a sufficient period of time for the ionic liquid to extract at least a portion of the sulfur-containing impurity from the hydrocarbon and following phase separation of the mixture of ionic liquid and hydrocarbon, the phases are physically separated from each other. The ionic liquid phase now comprises the sulfur-containing impurity and the hydrocarbon comprises a reduced amount of or no detectable amount of the impurity. The mass ratio of ionic liquid to hydrocarbon can vary widely but is generally in the range of about 1:1,000,000 to 999:1. Variation of the molar or weight ratio will depend upon the identity and physical properties of the hydrocarbon and ionic liquid, the amount or concentration of impurity(ies) present, and the solubility of the impurity(ies) within each the hydrocarbon and the ionic liquid.

Example 2

Exemplary Ionic Liquids of the Invention

An ionic liquid according to the invention is defined as a compound or mixture of compounds of the Formula 1 $(A)_n^+$ $(Y)^{n-}$. Exemplary ionic liquids according to the invention include, by way of example and without limitation (a) 1-Butyl-3-methylimidazolium tetrachloroaluminate; (b) 1-ethyl-3-methylimidazolium tetrachloroaluminate; (c) diethylcyclohexylammonium methanesulfonate/tributylammonium methylmethanesulfonate; (d) dodecyltrimethylammonium tetrachloroaluminate; (e) trioctylmethylammonium tetrachloroaluminate; (f) diethylmethylcyclohexylammonium methansulfonate/tributylmethylammonium methanesulfonate; (g) 1-butyl-3-methylimidazolium BTA; and (h) 1,3-dimethylimidazolium methanesulfonate.

Example 3

Desulfurization of N-Dodecane by Removal of Dibenzothiophene

The following general procedure is used for the desulfurization of n-dodecane. A solution comprising dibenzothiophene (present at a concentration of 500 ppm) dissolved in n-dodecane is provided. The n-dodecane is treated with an ionic liquid (selected from those of Example 2: (a) through (h)) by employing a single extraction. A mass ratio of 1 to 5 (ionic liquid: n-dodecane) was used. Mixing was conducted for 15 minutes at room temperature or at 60° C. in the case of (c) and (f) since these are solids at room temperature. The n-dodecane was separated from the two-phase mixture, and the sulfur content determined by combustion analysis. The chemical structure of some of the ionic liquids employed is show below. Below each structure is the concentration of dibenzothiophene remaining in the n-dodecane after the single extraction.

(a)

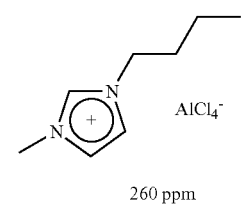

260 ppm (b)

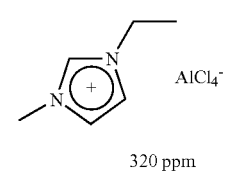

320 ppm (c)

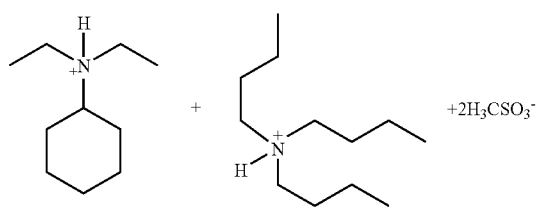

305 ppm (d)

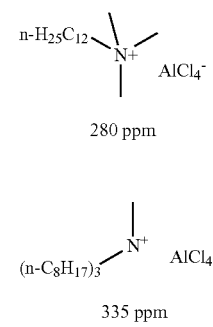

280 ppm (e)

(n-C$_8$H$_{17}$)$_3$N$^+$—  AlCl$_4^-$ 335 ppm (f)

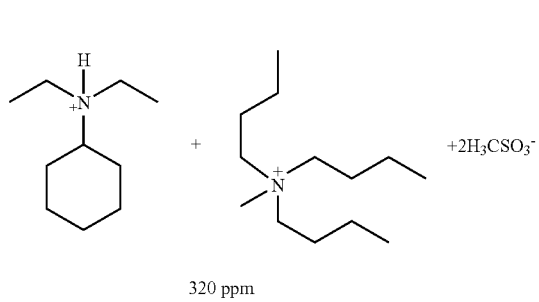

320 ppm (g)

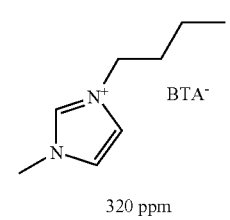

320 ppm

-continued (h)

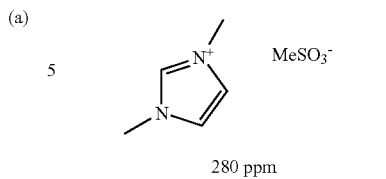

280 ppm

Example 4

Multistep Desulfurization of N-Dodecane by Removal of Dibenzothiophene

The following general procedure is used for the desulfurization of n-dodecane by employing multiple extractions.

Here it is shown that a further significant reduction of the sulfur content of the model component dibenzothiophene can be achieved by means of a multistep extraction with ionic liquids. Furthermore it is shown that the different ionic liquids in part have clearly different suitabilities. The process itself is the same as in Example 3. However, the model oil having been desulfurized once is again treated with fresh ionic liquid in second, third and optionally more other extraction steps. The results are shown in the following table.

| Results of multistep extractions of model oil (500 ppm) with ionic liquids | | | | |
|---|---|---|---|---|
| Ionic Compound | Sulfur content (ppm) after step | | | |
|  | 1$^{st}$ extrac. | 2$^{nd}$ extrac. | 3$^{rd}$ extrac. | 4$^{th}$ extrac. |
| (a) | 260 | 120 | 55 | 25 |
| (c) | 305 | 195 | 120 | 65 |
| (f) | 335 | 210 | 130 | 85 |
| (h) | 450 | 420 | 405 |  |

Example 5

Desulfurization of Fuels

The following general procedure is used for the desulfurization of fuels by employing multiple extractions. The following data show that a transfer of the experiments with the model component dibenzothiophene on the desulfurization with ionic liquids to complex real systems is possible. Thus, the same procedure is employed as in Example 4. As an example of a fuel, a predesulfurized diesel fraction with a sulfur content of 375 ppm is used. Some results are summarized in the following table.

| Results of multistep extractions of diesel fuel (375 ppm) with ionic liquids | | | | | |
|---|---|---|---|---|---|
| Ionic Compound | Sulfur content (ppm) after step | | | | |
|  | 1$^{st}$ extrac. | 2$^{nd}$ extrac. | 3$^{rd}$ extrac. | 4$^{th}$ extrac. | 8$^{th}$ extrac. |
| (a) | 220 | 160 | 130 | 100 | 40 |
| (c) | 325 | 290 | 250 | 225 |  |
| (f) | 330 | 300 |  |  |  |

Example 6

Purification of a Combination of Hydrocarbons

A mixture of hydrocarbons is purified according to the process of any one of examples 1-5 with the exception that a mixture of two or more hydrocarbons are used. The mixture is treated with an ionic liquid at a temperature between −150° to 500° C. for a period of time sufficient to extract polar impurity(ies) from the mixture. The phases of the extraction milieu are separated and the purified mixture of hydrocarbons is obtained.

Example 7

Purification of a Hydrocarbon with a Mixture of Ionic Liquids

A hydrocarbon or mixture of hydrocarbon is purified according to the process of any one of examples 1-5 with the exception that a mixture of two or more ionic liquids is used. The hydrocarbon is treated with a mixture of at least two different ionic liquids at a temperature between −150° to 500° C. for a period of time sufficient to extract polar impurity(ies) from the mixture. The phases of the extraction milieu are separated and the purified hydrocarbon is obtained.

Example 8

Purification of a Hydrocarbon Containing a Mixture of Polar Impurities

A hydrocarbon or mixture of hydrocarbon containing a mixture of polar impurities is purified according to the process of any one of examples 1-7. The mixture of polar impurities can comprise one or more sulfur-containing compounds, one or more nitrogen containing compounds, one or more oxygen-containing compounds, one or more halogen-containing compounds, or a mixture thereof. Extraction of the impurities from the hydrocarbon results in a decreased concentration of two or more of the polar impurities in the hydrocarbon. The concentration of each impurity can be reduced independently of another impurity in the hydrocarbon. The composition of the ionic liquid can be tailored to selectively or specifically extract one or more of the impurities; likewise it can be tailored to extract all of the impurities.

Example 9

Purification of a Hydrocarbon by Extraction with a Mixture of Extractants

A hydrocarbon or mixture of hydrocarbon containing one or more polar impurities is purified according to the process of any one of examples 1-8; with the exception that a mixture of extractants is used. The mixture of extractants comprises one or more ionic liquids and one or more other extractants as defined herein. The properties of the mixture of extractants can be tailored to selectively or specifically extract one or more of the impurities; likewise it can be tailored to extract all of the impurities. The properties of the mixture of extractants can also be tailored to enhance the immiscibility of hydrocarbon(s) and ionic liquid(s).

Example 10

Regeneration of Ionic Liquids

The ionic liquids can be regenerated after their use as extraction medium. This was demonstrated by using mixtures of dodecane with model sulphur and/or nitrogen substances (e.g. dibenzothiophene and indole) as well as with ionic liquids after their use to extract sulphur components from FCC-gasoline and diesel oil:

(1) FCC-gasoline with a sulphur content of 360 ppmw (mainly thiophene derivatives) was mixed vigorously with the ionic liquid (EMIM)(EtSO4) (1-ethyl-3-methylimidazolium ethanesulfonate) and also in a separate experiment with (BMIM)(OcSO4) (1-butyl-3-methylimidazolium octanesulfonate). After this extraction step, the sulphur loaded ionic liquid (50 ppm sulfur in case of EMIM-IL and about 60 ppm sulfur in case of BMIM-IL) were stripped with air for 2 hours at 100° C. After this regeneration no sulphur could be detected in the IL (as determined by re-extraction with cyclohexane and subsequent elemental analysis). (IL is taken to mean ionic liquid.)

(2) In case of diesel oil, the stripping procedure of item (1) above is possible, but takes much more time because of the much higher vapour pressure of the respective sulphur components in diesel oil (mainly dibenzothiophene derivatives), e.g. stripping with air at 120° C. for 3 days only leads to a regeneration degree of about 20% sulphur. So, the regeneration is preferably done by re-extraction. Diesel oil, having a sulphur content of 284 ppm of mainly dibenzothiophene derivatives, was vigorously mixed with the IL (BMIM)(OcSO4). After this extraction step, the sulphur loaded IL (70 ppm S) was re-extracted with cyclohexane in five subsequent re-extraction steps (each step with a mass ratio of IL to cyclohexane of 1/1 at 20° C.). After this regeneration procedure, no sulphur could be detected in the IL (as determined by elemental analysis of the final cyclohexane sample and an overall mass balance).

The disclosures of the references cited herein are hereby incorporated in their entirety.

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except by the appended claims. All of the embodiments disclosed and claimed herein can be made and executed without undue experimentation in light of the present disclosure.

We claim:

1. A process for the purification of a hydrocarbon, or mixture of hydrocarbons, comprising one or more impurities that are extractable with an ionic liquid, the process comprising the steps of:
   a) providing a hydrocarbon, or mixture of hydrocarbons, comprising one or more impurities that are extractable with an ionic liquid;
   b) exposing the hydrocarbon, or mixture thereof, to an ionic liquid while agitating for a period of time sufficient and at a temperature sufficient for the ionic liquid to extract at least a portion of the one or more impurities from the hydrocarbon and to form an at least biphasic mixture with the hydrocarbon, or mixture thereof; and
   c) separating the ionic liquid from the hydrocarbon, or mixture thereof, whereby the amount of one or more impurities in the hydrocarbon, or mixture thereof, is reduced; wherein:

the ionic liquid is a compound, or a mixture of compounds, of the Formula 1

, Formula 1 wherein:

n=1 or 2;

the anion $(Y)^{n-}$ is selected from the group consisting of tetrafluoroborate $((BF_4)^-)$, tetrachloroborate $((BCl_4)^-)$, hexafluorophosphate ((PF$_6$)$^-$), hexafluoroantimonate ((SbF$_6$)$^-$), hexafluoroarsenate ((AsF$_6$)$^-$), tetrachloroaluminate ((AlCl$_4$)$^-$), trichlorozincate ((ZnCl$_3$)$^-$), dichlorocuprate, sulfate ((SO$_4$)$^{2-}$), carbonate ((CO$_3$)$^{2-}$), fluorosulfonate, (R'—COO)$^-$, (R'—SO$_4$)$^-$, (R'—SO$_3$)$^-$ or ((R'—SO$_2$)$_2$N)$^-$, wherein R' is a linear or branched aliphatic or alicyclic alkyl containing from 1 to 16 carbon atoms, or a C$_5$-C$_{18}$ aryl, C$_5$-C$_{18}$-aryl-C$_1$-C$_6$-alkyl or C$_1$-C$_6$-alkyl-C$_5$-C$_{18}$-aryl residue which may be substituted with halogen atoms;

the cation (A)$^+$ is selected from the group consisting of
quaternary ammonium cations of general formula

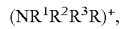

phosphonium cations of general formula

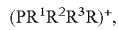

imidazolium cations of general formula

wherein the imidazole nucleus may be substituted with at least one group selected from C$_1$-C$_6$ alkyl, C$_1$-C$_6$ alkoxy, C$_1$-C$_6$ aminoalkyl, C$_5$-C$_{16}$ aryl or C$_5$-C$_{16}$-aryl-C$_1$-C$_6$-alkyl groups;

pyridinium cations of general formula

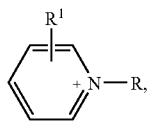

wherein the pyridine nucleus may be substituted with at least one group selected from C$_1$-C$_6$ alkyl, C$_1$-C$_6$ alkoxy, C$_1$-C$_6$ aminoalkyl, C$_5$-C$_{16}$ aryl or C$_5$-C$_{16}$-aryl-C$_1$-C$_6$-alkyl groups;

pyrazolium cations of general formula

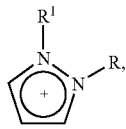

wherein the pyrazole nucleus may be substituted with at least one group selected from C$_1$-C$_6$ alkyl, C$_1$-C$_6$ alkoxy, C$_1$-C$_6$ aminoalkyl, C$_5$-C$_{16}$ aryl or C$_5$-C$_{16}$-aryl-C$_1$-C$_6$-alkyl groups; and triazolium cations of general formula

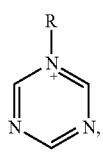

wherein the triazole nucleus may be substituted with at least one group selected from C$_1$-C$_6$ alkyl, C$_1$-C$_6$ alkoxy, C$_1$-C$_6$ aminoalkyl, C$_5$-C$_{16}$ aryl or C$_5$-C$_{16}$-aryl-C$_1$-C$_6$-alkyl groups;

the residues R$^1$, R$^2$, R$^3$ are independently selected at each occurrence from the group consisting of:
hydrogen;
linear or branched, saturated or unsaturated, aliphatic or alicyclic alkyl groups having from 1 to 20 carbon atoms;
heteroaryl, heteroaryl-C$_1$-C$_6$-alkyl groups having from 3 to 8 carbon atoms in the heteroaryl residue and at least one heteroatom selected from N, O and S which may be substituted with at least one group selected from C$_1$-C$_6$ alkyl groups and/or halogen atoms; and
aryl, aryl-C$_1$-C$_6$-alkyl groups having from 5 to 16 carbon atoms in the aryl residue which may be optionally substituted with at least one C$_1$-C$_6$ alkyl group and/or halogen atom; and
the residue R is independently selected at each occurrence from the group consisting of:
linear or branched, saturated or unsaturated, aliphatic or alicyclic alkyl groups having from 1 to 20 carbon atoms;
heteroaryl, heteroaryl-C$_1$-C$_6$-alkyl groups having from 3 to 8 carbon atoms in the heteroaryl residue and at least one heteroatom selected from N, O and S which may be substituted with at least one group selected from C$_1$-C$_6$ alkyl groups and/or halogen atoms;
aryl, aryl-C$_1$-C$_6$-alkyl groups having from 5 to 16 carbon atoms in the aryl residue which may be optionally substituted with at least one C$_1$-C$_6$ alkyl group and/or halogen atom;
wherein the one or more impurities is selected from the group consisting of nitrogen-containing impurities; halogen-containing impurities; oxygen-containing impurities, said oxygen-containing impurities being selected from the group consisting of aldehydes, ketones, carboxylic acids and peroxides; and a mixture of two or more thereof;
provided that when the cation (A)$^+$ is quaternary ammonium cations of general formula

the residues R$^1$, R$^2$, R$^3$ are independently selected at each occurrence from the group consisting of:
linear or branched, saturated or unsaturated, aliphatic or alicyclic alkyl groups having from 1 to 20 carbon atoms;
heteroaryl, heteroaryl-C$_1$-C$_6$-alkyl groups having from 3 to 8 carbon atoms in the heteroaryl residue and at least one heteroatom selected from N, O and S which may be substituted with at least one group selected from C$_1$-C$_6$ alkyl groups and/or halogen atoms; and
aryl, aryl-C$_1$-C$_6$-alkyl groups having from 5 to 16 carbon atoms in the aryl residue which may be optionally substituted with at least one C$_1$-C$_6$ alkyl group and/or halogen atom.

2. The process of claim 1, wherein (Y) is selected from the group consisting of alkylsulfonate, arylsulfonate, arylalkylsulfonate, alkoxysulfonate and alkylarylsulfonate optionally substituted with one or more halogen atoms.

3. The process of claim 2, wherein the halogen atom is independently selected at each occurrence from fluorine, chlorine or bromine.

4. The process of claim 3, wherein (Y) is fluorinated.

5. The process of claim 4, wherein (Y) is a perfluorinated alkylsulfonate or perfluorinated arylsulfonate.

6. The process of claim 5, wherein (Y) is trifluoromethanesulfonate.

7. The process of claim 2, wherein (Y) is methanesulfonate, benzenesulfonate or toluenesulfonate.

8. The process of claim 1, wherein (Y) is selected from the group consisting of alkylcarboxylate, arylcarboxylate, arylalkylcarboxylate, alkoxycarboxylate and alkylarylcarboxylate optionally substituted with one or more halogen atoms.

9. The process of claim 8, wherein the halogen is independently at each occurrence from fluorine, chlorine or bromine.

10. The process of claim 9, wherein (Y) is fluorinated.

11. The process of claim 10, wherein (Y) is a perfluorinated alkylcarboxylate or a perfluorinated arylcarboxylate.

12. The process of claim 11, wherein (Y) is trifluoromethanecarboxylate.

13. The process of claim 8, wherein (Y) is acetate or benzoate.

14. The process of claim 1, wherein R' is a linear or branched aliphatic or alicyclic alkyl containing from 1 to 8 carbon atoms, or a $C_6$-$C_{10}$ aryl, $C_6$-$C_{10}$-aryl-$C_1$-$C_4$-alkyl or $C_1$-$C_4$-alkyl-$C_6$-$C_{10}$-aryl residue optionally substituted with one or more halogen atoms.

15. The process of claim 1, wherein the hydrocarbon is selected from the group consisting of gasoline, diesel, kerosene, oil, fuel oil, lubricating oil, shale oil, brake fluid, hydraulic fluid, power steering fluid, light atmospheric gas oil, crude oil, heavy atmospheric gas oil, vacuum gas oil, FCC light cycle oil, coker gas oil, and naphtha.

16. The process of claim 1, wherein the steps of exposing and separating are repeated.

17. The process of claim 1, wherein the mass ratio of ionic liquid to hydrocarbon, or mixture of hydrocarbons, is in the range of about 1:1,000,000 to about 999:1.

18. The process of claim 1, wherein the step of exposing is conducted while heating.

19. The process of claim 1, wherein the ionic liquid is a solid in the absence of added heat.

20. The process of claim 1, wherein the ionic liquid is a solid at <30° C.

21. The process of claim 1, wherein the ionic liquid is a liquid at >0° C.

22. The process of claim 1, wherein the step of exposing is conducted at a temperature of about −150° to 500° C.

23. The process of claim 1, wherein one or more of the steps is conducted in a mixer-settler unit, tray column, bubble column, packed column, disk separator, rotating disk column or vibrating plate column.

24. A purified hydrocarbon, or mixture of hydrocarbons, prepared according to the process of claim 1, wherein a hydrocarbon, or mixture thereof, comprising one or more impurities is treated with one or more ionic liquids to provide the purified hydrocarbon, or mixture of hydrocarbons, having a reduced amount of the one or more impurities.

25. An at least biphasic composition comprising a hydrocarbon, or mixture of hydrocarbons, one or more polar impurities, and one or more ionic liquids of the Formula 1 as defined in claim 1, wherein:
   a) a first phase comprises the hydrocarbon, or mixture of hydrocarbons;
   b) a second phase comprises the one or more ionic liquids; and
   c) the one or more polar impurities is located in the first phase, second phase or both phases, wherein the one or more polar impurities is selected from the group consisting of nitrogen-containing impurities; halogen-containing impurities; oxygen-containing impurities, said oxygen-containing impurities being selected from the group consisting of aldehydes, ketones, carboxylic acids and peroxides; and a mixture of two or more thereof.

26. The composition of claim 25, wherein the one or more ionic liquids is present as an extraction medium.

27. The composition of claim 25, wherein the one or more ionic liquid is present as a component in a reaction medium.

28. The process of claim 1, wherein (A) is selected from the group consisting of ($C_{12}$-$C_{18}$)Alkylpoly(3)oxyethyl-dihydroxy-ethylmethylammonium, trimethylphenylammonium, methyltrioctylammonium, benzyldimethyltetradecylammonium, tetrabutylphosphonium, trihexyl(tetradecyl)phosphonium, 3-butyl-1-methylimidazolium, 3-ethyl-1-methylimidazolium, N-butylpyridinium, N-ethylpyridinium, diethylpyrazolium, 1-ethyl-3-methylimidazolium, 1-butyl-3-methylimidazolium, 1-hexyl-3-methylimidazolium, 1-octyl-3-methylimidazolium, 1-decyl-3-methylimidazolium, 1-butyl-4-methylpyridinium, 1-butyl-3-methylpyridinium, 1-butyl-2-methylpyridinium, 1-butylpyridinium, 1-butylmethylimidazolium, nonylmethylimidazolium, butylmethylimidazolium, hexylmethylimidazolium, octylmethylimidazolium, 4-methylbutylpyridinium, triethylmethylammonium, butylmethylpyridinium, methylmethylimidazolium, ethylmethylimidazolium, butylmethylimidazolium and butylmethylimidazolium.

29. A process for the purification of a hydrocarbon, or mixture of hydrocarbons, comprising one or more impurities that are extractable with an organic ionic liquid, the process comprising the steps of:
   a) providing a hydrocarbon, or mixture of hydrocarbons, comprising one or more impurities that are extractable with an organic ionic liquid;
   b) exposing the hydrocarbon, or mixture thereof, to one or more organic ionic liquids while agitating for a period of time sufficient and at a temperature sufficient for the organic ionic liquid to extract at least a portion of the one or more impurities from the hydrocarbon and to form an at least biphasic mixture with the hydrocarbon, or mixture thereof; and
   c) separating the organic ionic liquid from the hydrocarbon, or mixture thereof, whereby the amount of one or more impurities in the hydrocarbon, or mixture thereof, is reduced; wherein
   d) the organic ionic liquid comprises one or more organic anions and one or more organic cations, and the identity of the organic anion and organic cation is independently selected at each occurrence;
   e) the one or more impurities is selected from the group consisting of nitrogen-containing impurities; halogen-containing impurities; oxygen-containing impurities, said oxygen-containing impurities being selected from the group consisting of aldehydes, ketones, carboxylic acids and peroxides; and a mixture of two or more thereof;
   f) the organic anion is selected from the group consisting of alkylsulfonate, arylsulfonate, arylalkylsulfonate, alkoxysulfonate, alkylarylsulfonate, alkylcarboxylate, arylcarboxylate, arylalkylcarboxylate, alkoxycarboxylate, alkylarylcarboxylate, acetate, benzoate and any member of the group optionally substituted with one or more halogen atoms; and
   g) the organic cation is selected from the group consisting of quaternary ammonium cation, phosphonium cation, imidazolium cation, pyrdinium cation, pyrazolium cation, and triazolium cation.

30. The process according to claim 1, wherein the one or more nitrogen-containing impurities is selected from the group consisting of ammonia, organic nitrogen compound, amide, amino acid, and N-heterocyclic compound.

31. The process according to claim 1, wherein the one or more halogen-containing impurities is selected from the group consisting of organochloride and inorganic chloride.

32. The process according to claim 29, wherein the one or more nitrogen-containing impurities is selected from the group consisting of ammonia, organic nitrogen compound, amide, amino acid, and N-heterocyclic compound.

33. The process according to claim 29, wherein the one or more halogen-containing impurities is selected from the group consisting of organochloride and inorganic chloride.

34. A process for the purification of a hydrocarbon, or mixture of hydrocarbons, comprising one or more impurities that are extractable with an organic ionic liquid, the process consisting essentially of:
   a) providing a hydrocarbon, or mixture of hydrocarbons, comprising one or more impurities that are extractable with an organic ionic liquid;
   b) exposing the hydrocarbon, or mixture thereof, to one or more organic ionic liquids while agitating for a period of time sufficient and at a temperature sufficient for the organic ionic liquid to extract at least a portion of the one or more impurities from the hydrocarbon and to form an at least biphasic mixture with the hydrocarbon, or mixture thereof; and
   c) separating the organic ionic liquid from the hydrocarbon, or mixture thereof, whereby the amount of one or more impurities in the hydrocarbon, or mixture thereof, is reduced; wherein
   d) the organic ionic liquid comprises one or more organic anions and one or more organic cations, and the identity of the organic anion and organic cation is independently selected at each occurrence; and
   e) the one or more impurities is one or more sulfur-containing impurities selected from the group consisting of organic aliphatic or aromatic sulfur compounds, mercaptane, thiophene, methylthiophene, or dibenzolthiophene;
wherein the ionic liquid is a compound, or a mixture of compounds, of the Formula 1

Formula 1 wherein:
n=1 or 2;
the anion $(Y)^{n-}$ is selected from the group consisting of alkylsulfonate, arylsulfonate, arylalkylsulfonate, alkoxysulfonate, alkylarylsulfonate, alkylcarboxylate, arylcarboxylate, arylalkylcarboxylate, alkoxycarboxylate, alkylarylcarboxylate, acetate, benzoate and any member of the group optionally substituted with one or more halogen atoms;
the cation $(A)^+$ is selected from the group consisting of
   quaternary ammonium cations of general formula $(NR^1R^2R^3R)^+$, phosphonium cations of general formula $(PR^1R^2R^3R)^+$, imidazolium cations of general formula

wherein the imidazole nucleus may be substituted with at least one group selected from $C_1$-$C_6$ alkyl, $C_1$-$C_6$ alkoxy, $C_1$-$C_6$ aminoalkyl, $C_5$-$C_{16}$ aryl or $C_5$-$C_{16}$-aryl-$C_1$-$C_6$-alkyl groups;

pyridinium cations of general formula

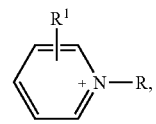

wherein the pyridine nucleus may be substituted with at least one group selected from $C_1$-$C_6$ alkyl, $C_1$-$C_6$ alkoxy, $C_1$-$C_6$ aminoalkyl, $C_5$-$C_{16}$ aryl or $C_5$-$C_{16}$-aryl-$C_1$-$C_6$-alkyl groups;
   pyrazolium cations of general formula

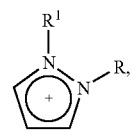

wherein the pyrazole nucleus may be substituted with at least one group selected from $C_1$-$C_6$ alkyl, $C_1$-$C_6$ alkoxy, $C_1$-$C_6$ aminoalkyl, $C_5$-$C_{16}$ aryl or $C_5$-$C_{16}$-aryl-$C_1$-$C_6$-alkyl groups; and
   triazolium cations of general formula

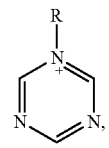

wherein the triazole nucleus may be substituted with at least one group selected from $C_1$-$C_6$ alkyl, $C_1$-$C_6$ alkoxy, $C_1$-$C_6$ aminoalkyl, $C_5$-$C_{16}$ aryl or $C_5$-$C_{16}$-aryl-$C_1$-$C_6$-alkyl groups;
the residues $R^1$, $R^2$, $R^3$ are independently selected at each occurrence from the group consisting of:
hydrogen;
linear or branched, saturated or unsaturated, aliphatic or alicyclic alkyl groups having from 1 to 20 carbon atoms;
heteroaryl, heteroaryl-$C_1$-$C_6$-alkyl groups having from 3 to 8 carbon atoms in the heteroaryl residue and at least one heteroatom selected from N, O and S which may be substituted with at least one group selected from $C_1$-$C_6$ alkyl groups and/or halogen atoms; and
aryl, aryl-$C_1$-$C_6$-alkyl groups having from 5 to 16 carbon atoms in the aryl residue which may be optionally substituted with at least one $C_1$-$C_6$ alkyl group and/or halogen atom; and
the residue R is independently selected at each occurrence from the group consisting of:
linear or branched, saturated or unsaturated, aliphatic or alicyclic alkyl groups having from 1 to 20 carbon atoms;
heteroaryl, heteroaryl-$C_1$-$C_6$-alkyl groups having from 3 to 8 carbon atoms in the heteroaryl residue and at least one heteroatom selected from N, O and S which may be substituted with at least one group selected from $C_1$-$C_6$ alkyl groups and/or halogen atoms;
aryl, aryl-$C_1$-$C_6$-alkyl groups having from 5 to 16 carbon atoms in the aryl residue which may be optionally substituted with at least one $C_1$-$C_6$ alkyl group and/or halogen atom.

35. The process of claim 34, wherein the halogen atom is independently selected at each occurrence from fluorine, chlorine or bromine.

36. The process of claim 35, wherein (Y) is fluorinated.

37. The process of claim 36, wherein (Y) is a perfluorinated alkylsulfonate or perfluorinated arylsulfonate.

38. The process of claim 37, wherein (Y) is trifluoromethanesulfonate.

39. The process of claim 34, wherein (Y) is methanesulfonate, benzenesulfonate or toluenesulfonate.

40. The process of claim 34, wherein (Y) is a perfluorinated alkylcarboxylate or a perfluorinated arylcarboxylate.

41. The process of claim 34, wherein (Y) is trifluoromethanecarboxylate.

42. The process of claim 34, wherein R' is a linear or branched aliphatic or alicyclic alkyl containing from 1 to 8 carbon atoms, or a $C_6$-$C_{10}$ aryl, $C_6$-$C_{10}$-aryl-$C_1$-$C_4$-alkyl or $C_1$-$C_4$-alkyl-$C_6$-$C_{10}$-aryl residue optionally substituted with one or more halogen atoms.

43. The process of claim 34, wherein the hydrocarbon is selected from the group consisting of gasoline, diesel, kerosene, oil, fuel oil, lubricating oil, shale oil, brake fluid, hydraulic fluid, power steering fluid, light atmospheric gas oil, crude oil, heavy atmospheric gas oil, vacuum gas oil, FCC light cycle oil, coker gas oil, and naphtha.

44. The process of claim 34, wherein the steps of exposing and separating are repeated.

45. The process of claim 34, wherein the mass ratio of ionic liquid to hydrocarbon, or mixture of hydrocarbons, is in the range of about 1:1,000,000 to about 999:1.

46. The process of claim 34, wherein the step of exposing is conducted while heating.

47. The process of claim 34, wherein the ionic liquid is a solid in the absence of added heat.

48. The process of claim 34, wherein the ionic liquid is a solid at <30° C.

49. The process of claim 34, wherein the ionic liquid is a liquid at >0° C.

50. The process of claim 34, wherein the step of exposing is conducted at a temperature of about −150° to 500° C.

51. The process of claim 34, wherein one or more of the steps is conducted in a mixer-settler unit, tray column, bubble column, packed column, disk separator, rotating disk column or vibrating plate column.

52. A purified hydrocarbon, or mixture of hydrocarbons, prepared according to the process of claim 34, wherein a hydrocarbon, or mixture thereof, comprising one or more impurities is treated with one or more ionic liquids to provide the purified hydrocarbon, or mixture of hydrocarbons, having a reduced amount of the one or more impurities.

53. The process of claim 1, wherein the ionic liquid is the sole extraction medium.

54. The process of claim 1, wherein the ionic liquid is present with one or more other extractants in an extraction mixture.

55. The process of claim 29, wherein the ionic liquid is the sole extraction medium.

56. The process of claim 29, wherein the ionic liquid is present with one or more other extractants in an extraction mixture.

57. The process of claim 34, wherein the ionic liquid is the sole extraction medium.

58. The process of claim 34, wherein the ionic liquid is present with one or more other extractants in an extraction mixture.

* * * * *